United States Patent
Bischoff et al.

(10) Patent No.: US 10,682,256 B2
(45) Date of Patent: *Jun. 16, 2020

(54) TREATMENT APPARATUS FOR OPERATIVELY CORRECTING DEFECTIVE VISION OF AN EYE, METHOD FOR GENERATING CONTROL DATA THEREFOR, AND METHOD FOR OPERATIVELY CORRECTING DEFECTIVE VISION OF AN EYE

(71) Applicant: Carl Zeiss Meditec AG, Jena (DE)

(72) Inventors: Mark Bischoff, Jena (DE); Gregor Stobrawa, Jena (DE); Wilfried Bissmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1094 days.

This patent is subject to a terminal disclaimer.

(21) Appl. No.: 14/804,943

(22) Filed: Jul. 21, 2015

(65) Prior Publication Data
US 2015/0366711 A1    Dec. 24, 2015

Related U.S. Application Data

(62) Division of application No. 12/742,201, filed as application No. PCT/EP2008/009247 on Nov. 3, 2008, now Pat. No. 9,084,667.

(30) Foreign Application Priority Data

Nov. 8, 2007   (DE) .................. 10 2007 053 281

(51) Int. Cl.
*A61F 9/008*     (2006.01)
*A61B 3/103*     (2006.01)

(52) U.S. Cl.
CPC .......... *A61F 9/00804* (2013.01); *A61F 9/008* (2013.01); *A61F 9/00827* (2013.01);
(Continued)

(58) Field of Classification Search
CPC .. A61F 9/008; A61F 9/00804; A61F 9/00827; A61F 9/00836; A61F 2009/00855; A61F 2009/00872; A61B 3/103
(Continued)

(56) References Cited

U.S. PATENT DOCUMENTS

| 4,842,599 A | 6/1989 | Bronstein |
| 5,549,632 A | 8/1996 | Lai |

(Continued)

FOREIGN PATENT DOCUMENTS

| CA | 2 620 095    | 4/2007 |
| CA | 2 620 095 A1 | 4/2007 |

(Continued)

OTHER PUBLICATIONS

Application and File History for U.S. Appl. No. 12/742,201, filed May 10, 2010. Inventors: Mark Bischoff et al.
(Continued)

*Primary Examiner* — Gary Jackson
*Assistant Examiner* — Sebastian X Lukjan
(74) *Attorney, Agent, or Firm* — Patterson Thuente Pedersen, P.A.

(57) ABSTRACT

A treatment apparatus for operatively correcting myopia or hyperopia in an eye includes a laser device controlled by a control device and that separates the corneal tissue by applying a laser beam. The control device controls the laser device to emit the laser beam into the cornea such that a lenticule-shaped volume is isolated in the cornea. The control device, when controlling the laser device, predefines the lenticule-shaped volume such that the volume has a minimum thickness of between 5 and 50 µm. For myopia correction, the minimum thickness occurs on the edge of the volume, and for hyperopia correction the minimum thickness occurs in the region of the visual axis.

33 Claims, 8 Drawing Sheets

(52) U.S. Cl.
CPC .......... *A61F 9/00836* (2013.01); *A61B 3/103* (2013.01); *A61F 2009/00855* (2013.01); *A61F 2009/00872* (2013.01)

(58) Field of Classification Search
USPC ............................................................ 606/5
See application file for complete search history.

(56) References Cited

U.S. PATENT DOCUMENTS

| | | | |
|---|---|---|---|
| 5,656,186 A | | 8/1997 | Mourou et al. |
| 5,984,916 A | | 11/1999 | Lai |
| 6,110,166 A | * | 8/2000 | Juhasz .................... A61F 9/008 128/898 |
| 6,325,792 B1 | | 12/2001 | Swinger et al. |
| 6,805,694 B2 | * | 10/2004 | Donitzky ................ A61F 9/008 128/898 |
| 9,084,667 B2 | * | 7/2015 | Bischoff ................. A61F 9/008 |
| 2001/0010003 A1 | | 7/2001 | Lai |
| 2003/0176855 A1 | | 9/2003 | Gross et al. |
| 2003/0212387 A1 | | 11/2003 | Kurtz et al. |
| 2004/0070761 A1 | | 4/2004 | Horvath et al. |
| 2004/0243112 A1 | * | 12/2004 | Bendett .............. A61F 9/00827 606/5 |
| 2006/0106371 A1 | | 5/2006 | Muhlhoff et al. |
| 2006/0155265 A1 | | 7/2006 | Juhasz et al. |
| 2006/0195075 A1 | | 8/2006 | Muhlhoff et al. |
| 2007/0088509 A1 | | 4/2007 | Cheng et al. |
| 2007/0179483 A1 | | 8/2007 | Muhlhoff et al. |
| 2015/0359674 A1 | * | 12/2015 | Bischoff ................. A61F 9/008 606/5 |

FOREIGN PATENT DOCUMENTS

| | | |
|---|---|---|
| DE | 695 00 997 T2 | 4/1998 |
| DE | 69433322 T2 | 9/2004 |
| DE | 10 2005 014 760 A1 | 10/2006 |
| DE | 699 32 809 T2 | 3/2007 |
| DE | 10 2005 049 281 A1 | 4/2007 |
| EP | 1 159 986 A2 | 12/2001 |
| EP | 1 666 009 A2 | 6/2006 |
| WO | WO 2004/032810 A2 | 4/2004 |
| WO | WO 2005/011545 A1 | 2/2005 |
| WO | WO 2005/011546 A1 | 2/2005 |

OTHER PUBLICATIONS

Lubatschowski et al., "Application of ultrashort laser pulses for intrastromal refractive surgery," Graefe's Arch Clin Exp Ophthalmol (2000), 238:33-39.

Vogel et al., "Factors determining the refractive effects of intrastromal photorefractive keratectomy with the picoseconds laser," J. Cataract Refract Surg., vol. 23, Nov. 1997, 1301-1310.

German Office Action for German Application No. 10 2007 053 281.6, dated Oct. 23, 2017.

* cited by examiner

FIG 1
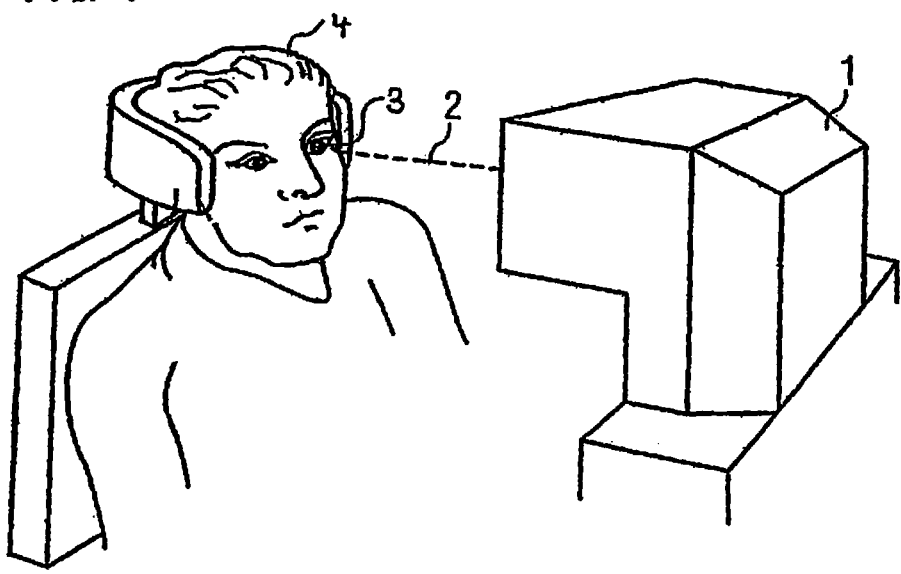
FIG 2
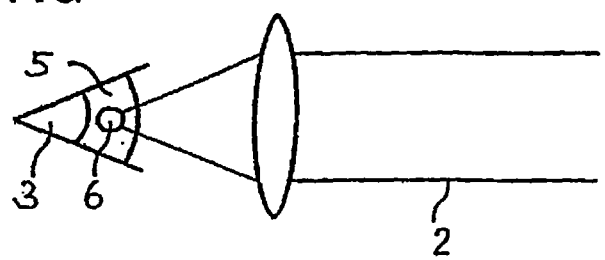
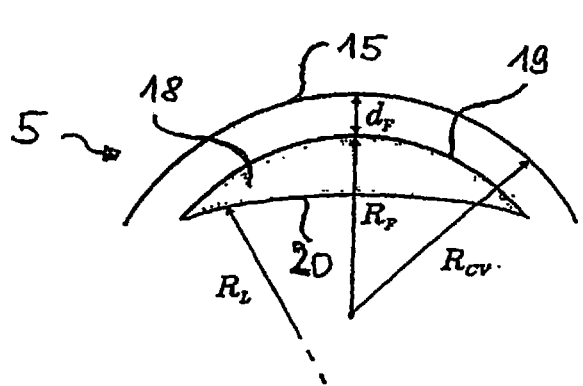
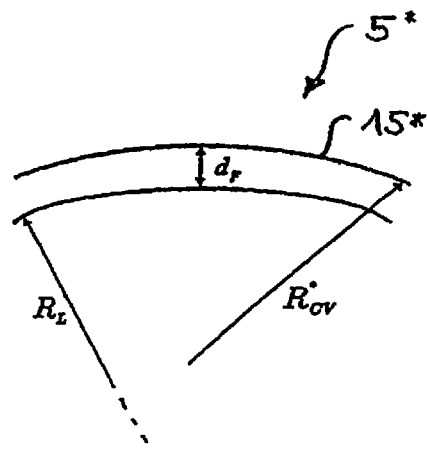
Fig. 5          Fig. 6

FIG 3
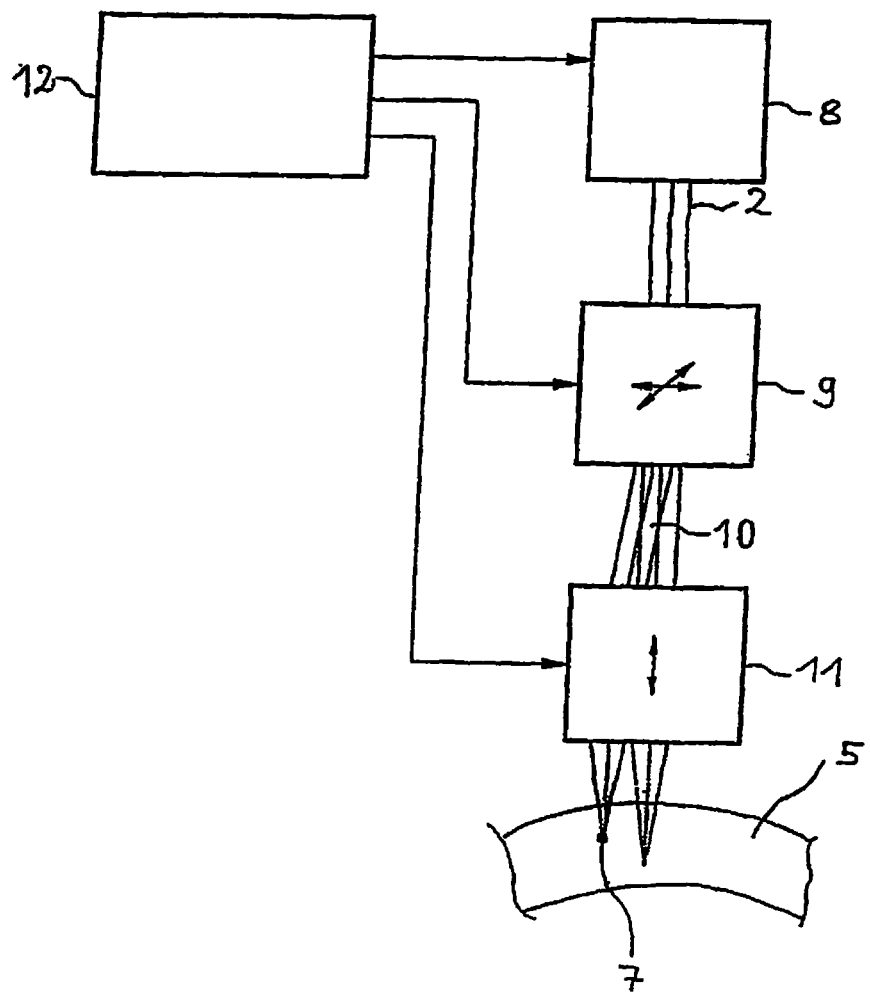
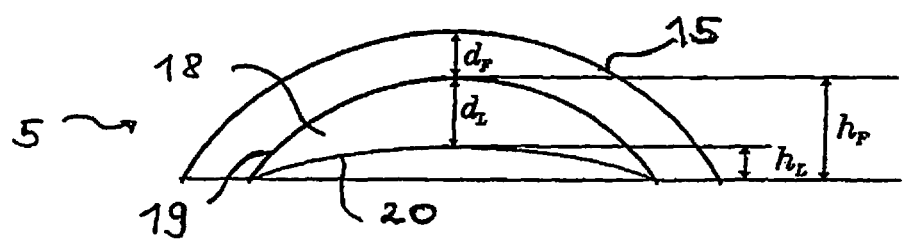
Fig. 7

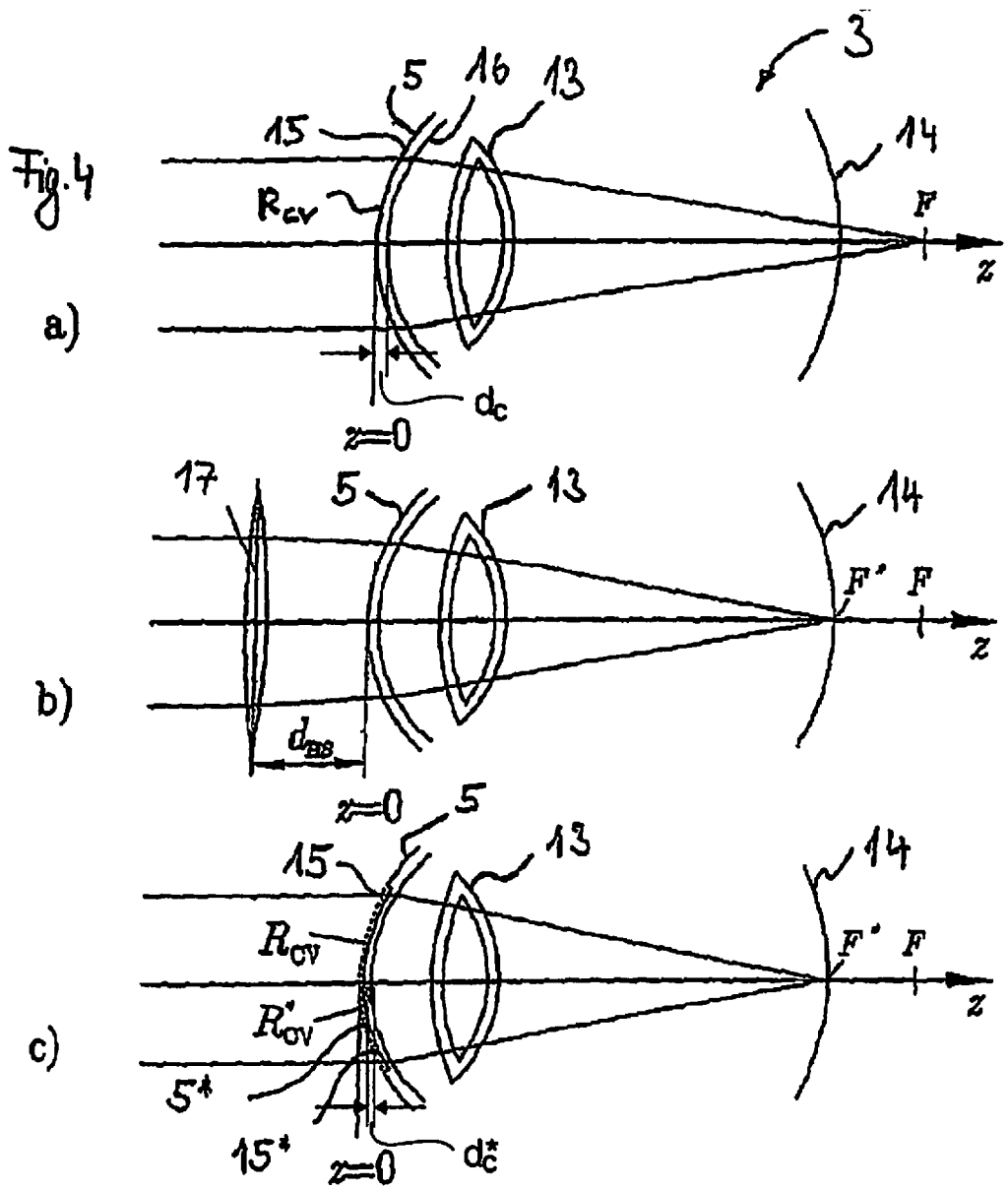
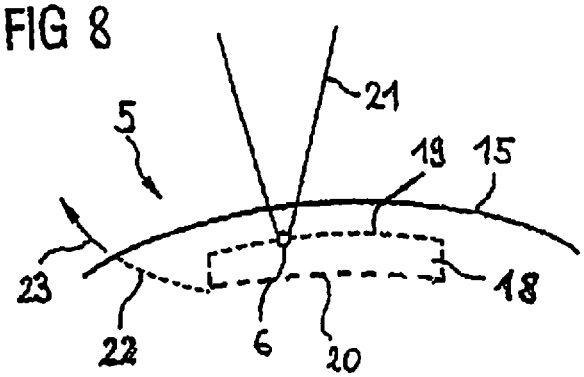

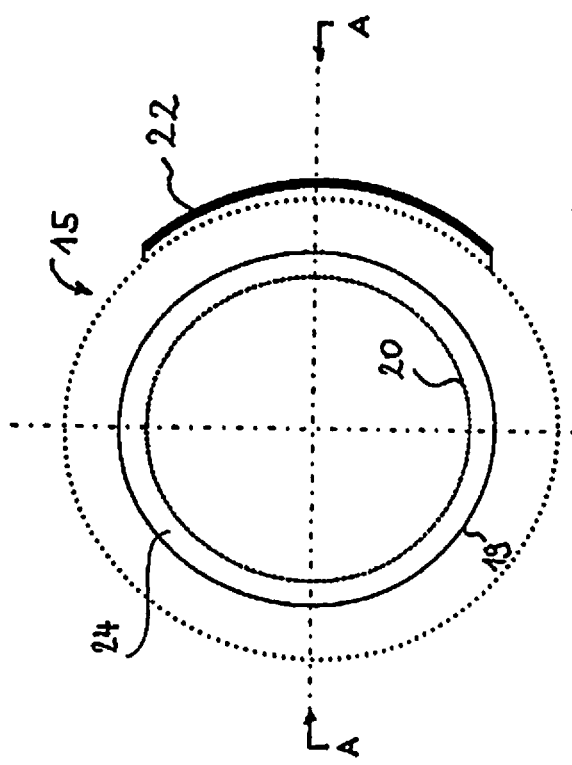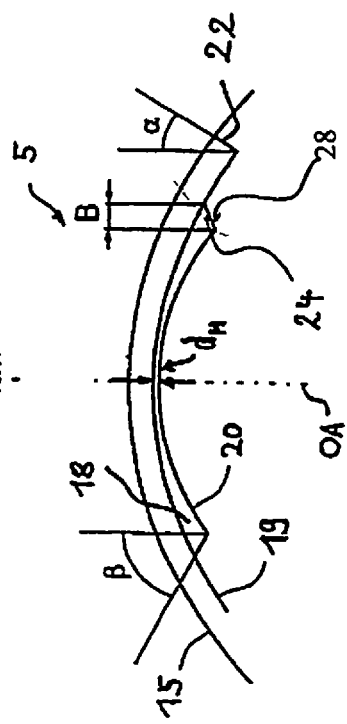
Fig. 9a
Fig. 9b

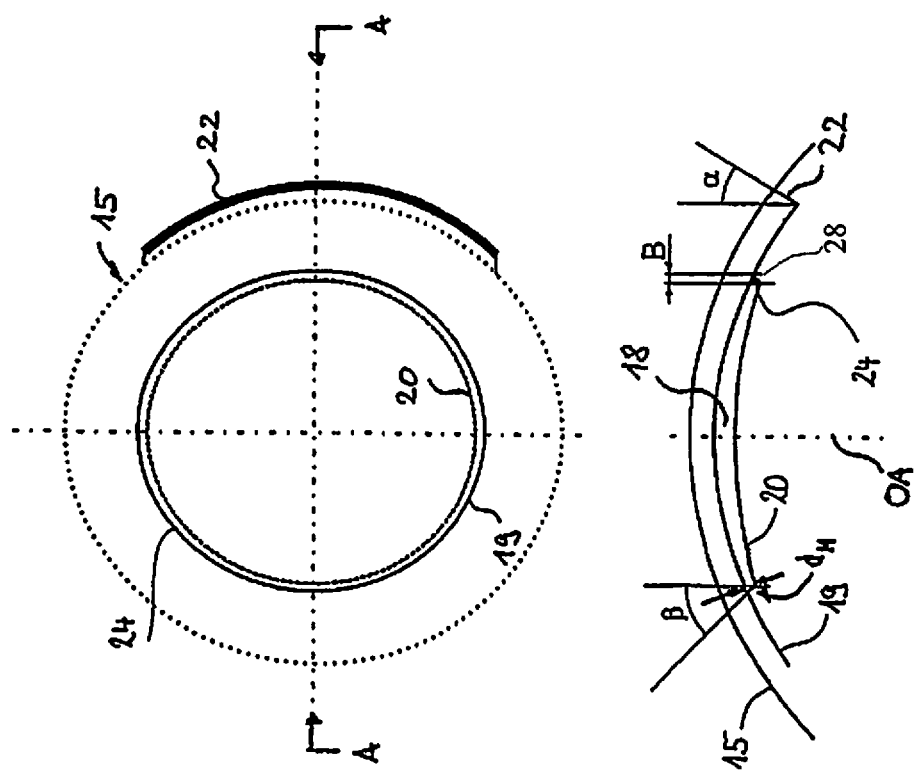

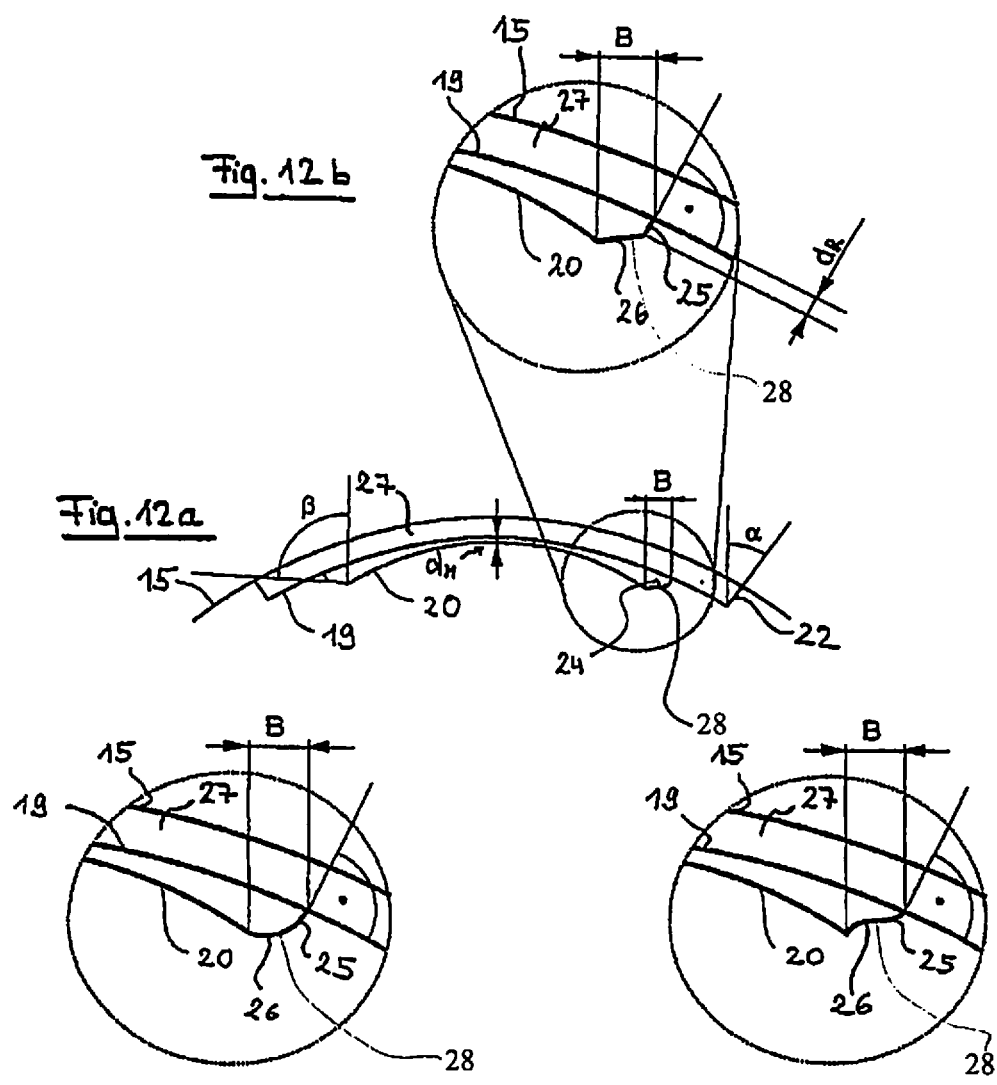

TREATMENT APPARATUS FOR OPERATIVELY CORRECTING DEFECTIVE VISION OF AN EYE, METHOD FOR GENERATING CONTROL DATA THEREFOR, AND METHOD FOR OPERATIVELY CORRECTING DEFECTIVE VISION OF AN EYE

RELATED APPLICATION

This application is a division of application Ser. No. 12/742,201, filed Sep. 3, 2010, which is a National Phase entry of PCT Application No. PCT/EP2008/009247, filed Nov. 3, 2008, which claims priority from German Application No. 102007053281.6, filed Nov. 8, 2007, each of which is hereby fully incorporated herein by reference.

FIELD OF THE INVENTION

The invention relates to a treatment apparatus for surgical correcting defective vision in the eye, the treatment apparatus having a laser device which is controlled by a control device and separates corneal tissue by applying laser radiation, the control device being adapted to control the laser device for emitting the laser radiation into the cornea in such a way that a lenticular volume is thus isolated in the cornea, the removal of which from the cornea effects the desired correction.

The invention further relates to a method for generating control data for a laser device of a treatment apparatus for operatively correcting defective vision in the eye, which laser device separates corneal tissue by applying laser radiation, wherein the control data control during operation the laser device for emitting the laser radiation into the cornea in such a way that a lenticular volume is thus isolated in the cornea, the removal of which from the cornea effects the desired correction.

Finally, the invention relates to a method for operatively correcting defective vision in the eye, corneal tissue being separated and a lenticular volume thus being isolated and removed in the cornea, the removal of which from the cornea effects the desired correction, by applying laser radiation.

BACKGROUND OF THE INVENTION

The conventional way to correct defective vision of the human eye is a pair of spectacles. However, meanwhile use is also increasingly being made of refractive surgery which effects a correction of defective vision by altering the cornea of the eye. The aim of the operating methods is in this case to alter the cornea selectively in order to influence the refraction of light. Different surgical methods are known for this purpose. Most widespread at present is what is known as laser-assisted in situ keratomileusis, which is also abbreviated to LASIK. In this case, a corneal lamella is firstly detached from the surface of the cornea on one side and folded to the side. This lamella can be detached by means of a mechanical microkeratome or else by means of what is known as a laser keratome, such as is sold by Intralase Corp. Irvine, USA, for example. Once the lamella has been detached and folded to the side, the LASIK operation provides the application of an excimer laser which removes by ablation the corneal tissue exposed in this way. Once the volume positioned in the cornea has been vaporised in this way, the corneal lamella is folded back to its original site.

The application of a laser keratome to expose the lamella (also referred to as a flap) is advantageous, as this reduces the risk of infection and increases the quality of the cut. In particular, the lamella can be produced at a very much more constant thickness. The cut is also potentially smoother; this reduces subsequent optical disturbances caused by this interface which remains even after the operation.

When generating a cut face in the cornea by laser radiation, conventionally pulsed laser radiation is introduced into the tissue, the pulse length being generally less than 1 ps. As a result, the power density, which is necessary for triggering an optical breakthrough, for the respective pulse is confined to a small spatial area. In this regard, U.S. Pat. No. 5,984,916 clearly discloses that the spatial region of the optical breakthrough (in this case the interaction generated) highly depends on the pulse duration. A high focusing of the laser beam in combination with the aforementioned short pulses thus allows the optical breakthrough to be employed with pinpoint accuracy in the cornea. For generating the cut, a series of optical breakthroughs is generated at predetermined points in such a way that the cut surface is formed as a result. In the aforementioned laser keratome, the cut surface forms the lamella which is to be folded down before the use of the laser ablation.

In the conventional LASIK method, exposed corneal tissue is vaporised; this is also referred to as "grinding" of the cornea by means of laser radiation. The removal of volume that is necessary for correcting defective vision is in this case set for each surface element of the exposed cornea by the number of laser pulses and the energy thereof. Different amounts of material are removed in accordance with the number and energy of the laser pulses.

SUMMARY OF THE INVENTION

Very recently, the operating method mentioned initially has been described and examined in first tests. Laser radiation is used to isolate a volume in the cornea and then to remove the piece of tissue forming this volume. As pulsed laser radiation is generally used in this case too, reference is made to femtosecond lenticule extraction or FLEx for short. The volume is referred to as the lenticule.

Now, experimental values which are suitable for grinding the cornea by means of ablation laser radiation cannot be used for the FLEx method of refractive eye surgery, in which the volume to be removed from the cornea is not removed by the ablation of exposed corneal tissue, but is isolated in the cornea by a three-dimensional cut face and thus made suitable for removal, as the approaches of vaporising material to be removed, on the one hand, and removing an isolated volume, on the other hand, are too different. This applies most particularly to the selection of the cut surface bounding the volume to be removed, as there is no such cut surface in the conventional LASIK operation. The healing processes after the operation are also different, as the faces have different surface structures.

Manual removal requires a certain mechanical stability of the piece of tissue that is, in addition to the intended refractive effect, a further requirement. In addition, there is the desire for shaping allowing the refractive effects of the healing processes to be minimised or at least to be made predictable.

If the isolated volume is destroyed (torn up) during manual extraction thereof, this would not in itself present any problem to the refractive effect. However, it is necessary to remove the isolated volume as completely as possible: a requirement which should be strictly adhered to, in particular in the optical relevant zone (projection of the opened pupil onto the cornea) in order to avoid optical aberrations later on. Tearing-up of the isolated volume would therefore be associated with major additional effort in the removal of a part of the isolated volume, is as a result also less safe and jeopardizes the success of a refractive therapy.

It is furthermore desirable to make refractive changes in the course of the healing processes (what is known as regression) as slight and predictable as possible.

Overall, there are thus in many areas different and in some cases also new requirements in the refractive correction of defective vision by means of FLEx compared to in the conventional LASIK method.

It is therefore the object of the present invention to provide a treatment apparatus or a method of the type mentioned at the outset in such a way that the cut faces for the lenticule are advantageous both for secure removal and for the healing process.

According to the invention, this object is achieved by a treatment apparatus for surgically correction of hyperopia in an eye, the treatment apparatus having a laser device which is controlled by a control device and separates corneal tissue by applying laser radiation, the control device being adapted to control the laser device for emitting the laser radiation into the cornea such that a lenticular volume is isolated in the cornea, the removal of which from the cornea effects a desired correction of hyperopia, wherein the lenticular volume has a posterior face and an anterior face, the edges of which are connected via an eye edge face, wherein a sectional curve made up of the edge face and a plane in which an axis of vision iof the eye lies has perpendicularly to the axis of vision a width which is greater than that which would have in the same projection plane a straight line which is perpendicular at the edge of the posterior or the anterior face on the respective face and connects the anterior face to the posterior face or to a notional or imaginary continuation thereof.

This object is further achieved by a method for generating control data for a laser device of a treatment apparatus for surgical correction of hyperopia in an eye, which laser device separates corneal tissue by applying laser radiation, wherein the control data control the laser device operation for emitting the laser radiation into the cornea such that a lenticular volume is isolated in the cornea, the removal of which from the cornea effects a desired correction of hyperopia, wherein the control data define the lenticular volume to have a posterior face and an anterior face, the edges of which are connected via an edge face, wherein a sectional curve made up of the edge face and a plane in which an axis of vision of the eye lies has perpendicularly to the axis of vision a width which is greater than that which would have in the same projection plane a straight line which is perpendicular at the edge of the posterior or the anterior face on the respective face and connects the anterior face to the posterior face or to a notional continuation thereof.

Finally, the object is also achieved by a method for surgical correction of hyperopia in an eye, wherein corneal tissue is separated by applying laser radiation and a lenticular volume is isolated and removed in the cornea, the removal of which volume effects a desired correction of hyperopia, wherein the lenticular volume provides a posterior face and an anterior face, the edges of which are connected via an edge face, wherein a sectional curve made up of the edge face and a plane in which an axis of vision of the eye lies has perpendicularly to the axis of vision a width which is greater than that which would have in the same projection plane a straight line which is perpendicular at the edge of the posterior or the anterior face on the respective face and connects the anterior face to the posterior face or to a notional continuation thereof.

The invention ensures that the volume to be removed, i.e. the piece of tissue isolated in the cornea of the eye, has sufficient stability, thus preventing with sufficient certainty tearing-off of parts of the piece of tissue during removing or removal from the cornea of the eye. The invention is in this case based on the finding that the tissue of the cornea of the eye becomes excessively fragile below a certain remaining thickness. According to the invention, the minimum thickness is set in the range of this remaining thickness. A minimum thickness in the range of from 5 to 50 µm ensures that the corneal tissue does not tear and thus prevents the formation of any undesirable particles which would cause poor optical quality if they were left in the cornea of the eye.

The problems of minimum thickness are presented both in a correction of hyperopia and in the correction of myopia. In the removal of a hyperopic lenticule, the minimum thickness is provided in the region of the axis of vision, i.e. in the central region of the lenticule. In a myopic lenticule, on the other hand, the minimum thickness is provided at the edge.

The inventors have found that it is advantageous for the overall optical quality of the correction to remove more volume than is required per se, i.e. to provide a minimum thickness for the lenticule. Surprisingly, this contradiction to basically all surgical interventions, which try in the case of internal wounds to be as economical as possible with tissue, leads to a better optical quality, as there is no risk of tissue fragments in the cornea of the eye. The approach according to the invention therefore drastically reduces the need for postoperative corrections. An embodiment of the invention additionally uses the minimum thickness to prevent that occurrence of in the FLEX method of postoperative (regression) problems occur due to detached and reapplied corneal lamella being disadvantageously inserted or being unable to rest smoothly at the edge of the removed volume. In order to avoid regression problems of this type, the invention provides a wide edge zone, thus producing for the corneal lamella, which merges there with the posterior cut face which was produced for isolating the lenticular volume, a transition zone causing almost no regression. If this transition zone is preferably also positioned outside the optically effective region, i.e. outside the dark-adapted pupil of the eye, the risk of further undesirable side effects is further reduced. Preferably, the transition zone has a width of between 0.1 and 1 mm.

It has further been found that regressions are particularly effectively reduced if the edge face opens as perpendicularly as possible into the anterior face. A course of this type is primarily surprising as, in the case of such perpendicular opening of the corneal lamella positioned here, even a step leading perpendicularly away from the anterior surface of the cornea can occur. This perpendicular opening on the one hand sets the minimum edge thickness and on the other hand has proven unproblematic with regard to regression if the edge face additionally has below this perpendicular opening a second portion, more inclined towards the axis of vision. As a result of this configuration, the lenticular volume has an edge thickness which is preferably between 5 and 50 µm. It has been found that an edge thickness of this type is unproblematic with regard to regression, but at the same time ensures that the piece of tissue can be removed more effectively, as the edge thickness prevents with sufficient certainty particles from becoming torn off from the edge when the piece of tissue is detached. Particles of this type influence the positioning of the corneal lamella after removal of the tissue much more intensively than does the comparatively lower edge thickness of the piece of tissue and thus the short, perpendicularly opening portion of the edge face. This configuration of the invention therefore takes an edge structure which at first sight appears negative and achieves therewith as a result lower regression, i.e. better ingrowth behavior, than an edge which is as narrow as possible which would actually be expected.

The second portion of the edge face, which is more inclined towards the axis of vision, can be embodied in many ways. One possible example is a straight course which runs at an angle to the first portion and is positioned at an angle of from 80° to 100° relative to the direction of the axis of vision. The second portion of the edge face can then be understood to be a chamfer. However, curved courses are also possible, for example a concave course based on the point of passage of the axis of vision, i.e. a curvature of the second portion toward the axis of vision. In this case, the second portion is then designed in the form of a rounding, for example.

Within the scope of the development of the invention, a broad range of geometries are suitable for the edge that all positively influence the regression behavior by providing the described wide transition zone.

In an embodiment of the invention, the edge structure is combined with a dimensioning rule for the volume of the cornea that defines the radius of curvature which the cornea has after the removal of the volume. This development of the invention therefore allows not only a regression-optimized edge structure, but also an analytical calculation of the posterior and the anterior face.

The description of the curvature of the front surface of the cornea after the correction starts in this case from defective vision data which specify the refractive power $B_{BR}$ of a pair of spectacles which are suitable for correcting defective vision and must be positioned at a distance $d_{HS}$ before the corneal apex in order to achieve the desired correction of defective vision. The determining of these parameters is an established standard in ophthalmology and allows the use of existing measuring appliances. It goes without saying that the measurement data used in this case can also represent astigmatism defects or defects of higher aberration orders, so that the equation for describing the radius of curvature of the cornea reduced by the volume then has corresponding angle parameters (based on cylindrical coordinates) as represented in the following Equation (1) of the description of the figures.

Preference is therefore given to an embodiment of the apparatus according to the invention or the method according to the invention in which the anterior face is positioned at a constant distance $d_F$ from the front surface of the cornea and the posterior face is curved and has a radius of curvature $R_L = R_{CV}^* - d_F$, wherein $R_{CV}^*$ satisfies the following equation $R_{CV}^* = 1/((1/R_{CV}) + B_{BR}/((n_c-1)\cdot(1-d_{HS}\cdot B_{BR}))) + F$, and $R_{CV}$ is the radius of curvature of the cornea before removal of the volume, $n_c$ is the refractive index of the material of the cornea, F is a correction factor, $B_{BR}$ is the refractive power of a pair of spectacles suitable for correcting defective vision, and also $d_{HS}$ is the distance at which the pair of spectacles having the refractive power $B_{BR}$ would have to be positioned before the corneal apex in order to achieve the desired correction of defective vision by means of the pair of spectacles.

The correction factor F is a measure of the optical effect of the reduction in thickness of the cornea of the eye on the axis of vision resulting from the removal of the volume. In a simplified calculation, the factor F may be set to zero. In a more accurate calculation, F may be calculated as follows: $F = (1 - 1/n_c) \cdot (d_C^* - d_C)$, wherein $d_C$ and $d_C^*$ respectively denote the thickness of the cornea before and after removal of the volume and the radius $R_{CV}^*$ can be calculated iteratively in that during each iteration step a change in thickness $(d_C^* - d_C)$ is concluded from the difference $(R_{CV}^* - R_{CV})$ and the corresponding result obtained therefrom for the change in thickness is applied in the calculation of $R_{CV}^*$ in the next iteration step. The iterative calculation for F can for example be terminated if a difference which is less than a specific limit value is all that remains for F between two iteration steps.

The configuration, provided in the embodiment, of the posterior face having a curvature which relates to that of the front surface of the cornea after the removal of the volume allows a particularly simple definition of the faces bounding the volume, as the anterior face is now positioned at a constant distance below the front surface of the cornea and the optical correction is effected by the shape of the posterior face. Notable computing effort then occurs only for the definition of the posterior face part, but not for the anterior face part. Furthermore, it has also been found that an approach of this type allows at the same time a simple analytical description of the posterior face part.

The method according to the invention for preparing the control data can be carried out without human participation. In particular, it can be executed by a computer which determines the control data from proper inputs, for example from measurement data of the eye. The participation of a doctor is in no way required above all when determining the control data, as no therapeutic intervention is as yet associated with determining the control data. Such intervention does not take place until the previously determining control data are applied.

In so far as this description has described method steps, the apparatus according to the invention contains a controller which takes care of the execution of the method steps during operation of the apparatus.

BRIEF DESCRIPTION OF THE DRAWINGS

The invention will be described in greater detail hereinafter by way of example with reference to the drawings, in which:

FIG. 1 is a schematic illustration of a treatment apparatus or a treatment device for correcting defective vision;

FIG. 2 is an illustration showing the principle for introducing pulsed laser radiation into the eye in the correction of defective vision using the treatment device of FIG. 1;

FIG. 3 is a further schematic illustration of the treatment device of FIG. 1;

FIG. 4 shows in subfigures (a), (b) and (c) schematic sectional illustrations to clarify the need for correction in the human eye in the case of defective vision;

FIG. 5 is a schematic sectional illustration through the cornea of the eye illustrating a volume to be removed for correcting defective vision;

FIG. 6 is a section through the cornea of the eye after removal of the volume of FIG. 5;

FIG. 7 is a sectional illustration similar to FIG. 5;

FIG. 8 is a schematic sectional illustration through the cornea of the eye to depict the removal of the volume;

FIG. 9a is a plan view onto the cornea of the eye to depict the cut faces generated during the correction of the defective vision;

FIG. 9b is a sectional illustration relative to the plan view of FIG. 9a, depicting the profile of a volume removed for the correction of hyperopia;

FIG. 10a is an illustration similar to FIG. 9a, but in this case for a correction of myopia;

FIG. 10b is an illustration similar to FIG. 9a, but again for correction of myopia;

FIG. 11a is an illustration similar to FIG. 9a, but with a different guidance of the cut with respect to the removal of the volume;

FIG. 11b is a sectional illustration similar to FIG. 9b, but for the plan view of FIG. 11a;

FIG. 12a is a sectional illustration similar to FIG. 9a, but with a different type of edge cut for bounding the volume which is removed for the correction of defective vision;

FIG. 12b is an enlarged partial view of the edge cut of FIG. 9a; and

FIGS. 12c and 12d are enlarged edge cut illustrations similar to FIG. 12b, but for different geometries of the edge face.

DETAILED DESCRIPTION OF THE DRAWINGS

FIG. 1 shows a treatment device 1 for an ophthalmic surgical method similar to that described in EP 1159986 A1 or U.S. Pat. No. 5,549,632. The treatment device 1 effects a correction of defective vision in an eye 3 of a patient 4 by means of a treatment laser radiation 2. The defective vision may include hyperopia, myopia, presbyopia, astigmatism, mixed astigmatism (astigmatism involving hyperopia in one direction and myopia in a direction lying at right angles thereto), aspherical defects and higher-order aberrations. The treatment laser radiation 2 is applied in the described embodiment as a pulsed laser beam focused into the eye 3. The pulse duration is in this case in the femtosecond range, for example, and the laser radiation 2 acts by means of non-linear optical effects in the cornea. The laser beam has for example 50 to 800 fs-short laser pulses (preferably 100-400 fs) having a pulse repetition frequency of between 10 and 500 kHz. In the exemplary embodiment described, the assemblies of the device 1 are controlled by an integrated control unit, although this unit can of course also be embodied in a stand-alone manner.

Before the treatment device is used, the defective vision of the eye 3 is measured using one or more measuring devices.

Figure 1A:
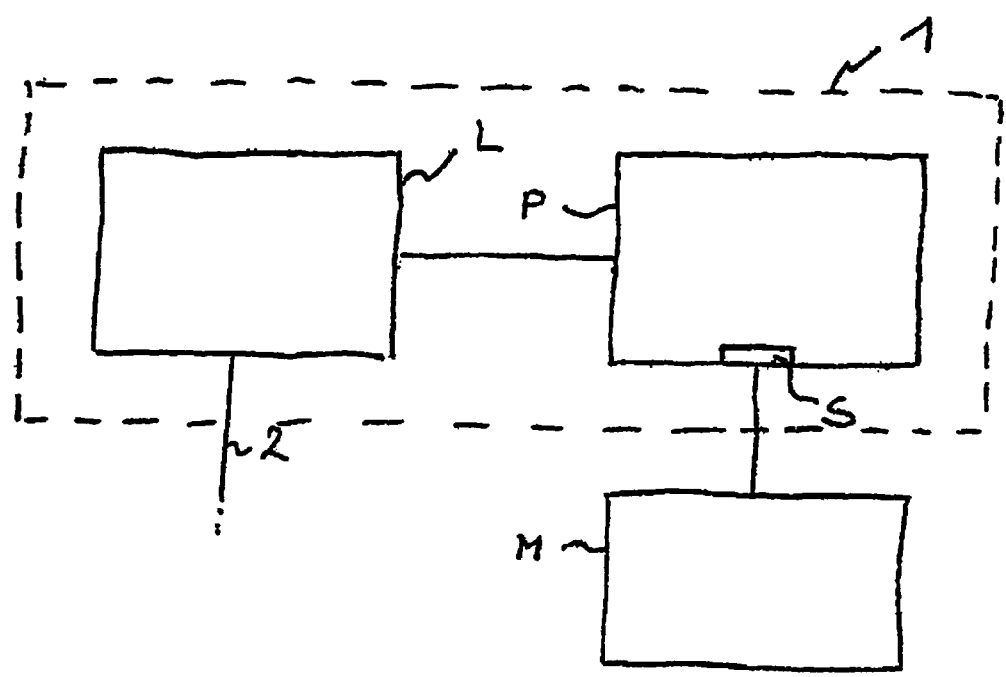
FIG. 1a is a schematic illustration with regard to the construction of the treatment device of FIG. 1.

FIG. 1a shows schematically the treatment device 1. In this variant, the treatment device has at least two sub-devices or modules. A laser device L emits the laser beam 2 to the eye 3. The laser device L in this case operates fully automatically, i.e. the laser device L starts, on a corresponding start signal to shift the laser beam 2 and generates in this manner cut faces which are constructed in a manner to be described hereinafter and isolate a volume in the cornea of the eye. The laser device L receives beforehand via control lines which will not be designated in greater detail from a planning device P control data required for operation as a set control data. The transmission takes place before operation of the laser device L. It is of course also possible to communicate wirelessly. As an alternative to direct communication, it is also possible to arrange the planning unit P spatially separated rom the laser unit L and to provide a corresponding data transmission channel.

Preferably, the set of control data is transmitted to the treatment device 1 and, also preferably, an operation of the laser device L is blocked until a valid set of control data is present on the laser device L. A valid set of control data may be a set of control data which is in principle suitable for use with the laser device L of the treatment device 1. In addition, validity can also be linked to further tests being passed, for example whether particulars, which are additionally filed in the set of control data, about the treatment device 1, for example an device serial number, or about the patient, for example a patient identification number, correspond to other particulars which were for example read out from the treatment device or separately input as soon as the patient is in the correct position for operation of the laser device L.

The planning unit P generates the set of control data, which is provided to the laser unit L for executing the surgical operation, from measurement data and defective vision data which were acquired for the eye to be treated. They are supplied to the planning unit P via an interface S and originate in the illustrated example embodiment from a measuring device M which previously measured the eye of the patient 4. Of course, the measuring device M can transmit the corresponding measurement and defective vision data to the planning unit P in any desired manner.

The data can be transmitted by memory chips (for example by a USB or memory stick), magnetic memories (for example floppy disks), by radio (for example WLAN, UMTS, Bluetooth) or in a hard wired manner (for example USB, FireWire, RS232, CAN Bus, Ethernet, etc.). Of course, the same applies with regard to the transmission of data between the planning unit P and laser device L.

A direct radio or wired connection of the measuring device M to the treatment device 1 with regard to the transmission of data, which can be used in a variant, has the advantage that the use of false measurement and defective vision data is ruled out with maximum possible certainty. This applies in particular when the patient is transferred from the measuring device M or measuring devices to the laser device L by means of a bed device (not shown in the figure) which interacts with the measuring device M or the laser device L in such a way that the respective devices detect whether the patient 4 is in the proper position for measuring or introducing the laser radiation 2. In this case, the measurement and defective vision data can be transmitted to the treatment apparatus 1 at the same time as the patient 4 is transferred from the measuring device M to the laser device L.

Suitable means preferably ensure that the planning unit P always generates the set of control data pertaining to the patient 4 and the risk of an erroneous use of an incorrect set of control data for a patient 4 is all but ruled out.

The effect of the laser beam 2 is indicated schematically in FIG. 2. The treatment laser beam 2 is focused into the cornea 5 of the eye 6 by means of optics which are not be designated. This produces in the cornea 5 a focus which covers a spot 6 and in which the laser radiation energy density is so high that a non-linear effect occurs in the eye in combination with the pulse length. For example, each pulse of the pulsed laser radiation 2 can generate at the respective spot 6 an optical breakthrough in the cornea 5 of the eye, which breakthrough in turn initiates a plasma bubble indicated schematically in FIG. 2. As a result, tissue is separated in the cornea 5 this laser pulse. When a plasma bubble is produced, the tissue layer separation comprises a larger area than the spot 6 which the focus of the laser radiation 2 covers, although the conditions for generating the breakthrough are achieved only in the focus. In order for an optical breakthrough to be generated by each laser pulse, the energy density, i.e. the fluence of the laser radiation, must be above a certain, pulse length-dependent threshold value. This relationship is known to the person skilled in the art from DE 69500997 T2, for example.

Alternatively, a tissue-separating effect of the pulsed laser radiation can also be generated in that a plurality of laser radiation pulses are emitted in a region, the spots 6 overlapping for a plurality of laser radiation pulses. A plurality of laser radiation pulses then co-operate to achieve a tissue-separating effect.

However, the type of tissue separation which the treatment device 1 uses is not relevant for the following description; all that matters is that treatment laser radiation 2 pulsed is used. For example, use may be made of a treatment device 1 such as is described in WO 2004/032810 A2. It is also essential that a large number of laser pulse foci form a cut face in the tissue, the shape of which is dependent on the pattern in which the laser pulse foci are/become arranged in the tissue. The pattern predefines target points for the position of the focus, at which points one or more laser pulse(s) is/are emitted, and defines the shape and position of the cut face. The pattern of the target points is important for the methods and apparatuses described hereinafter and the pattern will be described in greater detail below.

In order now to execute a correction of defective vision, material is removed from an area within the cornea 5 by means of the pulsed laser radiation by separating the layers of tissue which isolate the material and then allow the material to be removed. The removal of material effects a change in volume in the cornea resulting in a change in the optical imaging effect of the cornea 5, the dimensions of which are precisely such that the previously determined defective vision is/becomes thereby corrected as far as possible. For isolating the volume to be removed, the focus of the laser radiation 2 is directed toward target points in the cornea 5, generally in a region positioned below the epithelium and the Bowman's membrane and also above the Descemet's membrane and the endothelium. For this purpose, the treatment device has a mechanism for shifting the position of the focus of the laser radiation 2 in the cornea 5. This is shown schematically in FIG. 3.

Elements of the treatment device 1 are included in FIG. 3 only in so far as they are required to understand the shifting of the focus. The laser radiation 2 is, as mentioned hereinbefore, focused to a focus 7 in the cornea 5, and the position of the focus 7 in the cornea is shifted, so that for generating the cut face at various points focussed energy from laser radiation pulses is introduced into the tissue of the cornea 5. The laser radiation 2 is provided as pulsed radiation by a laser 8. An xy scanner 9, which is embodied in a variant by two galvanometer mirrors deflecting about substantially orthogonally axes, two-dimensionally deflects the laser beam coming from the laser 8, so that after the xy scanner 9 a deflected laser beam 10 is present. The xy scanner 9 thus effects a shifting of the position of the focus 7 substantially perpendicularly to the main direction of incidence of the laser radiation 2 into the cornea 5. In addition to the xy scanner 9, a z scanner 11, which is embodied as an adjustable telescope for example, is provided for adjusting the depth position. The z scanner 11 provides for the z position of the focus 7, i.e. the position thereof on the optical axis of incidence, being shifted. The z scanner 11 can be arranged downstream or upstream of the xy scanner 9. The coordinates denoted hereinafter by x, y, z therefore relate to the shifting of the position of the focus 7.

The allocation of the individual coordinates to the spatial directions is not essential for the functioning principle of the treatment appliance 1; however, for the sake of simplicity of description, z denotes hereinafter in all cases the coordinates along the optical axis of incidence of the laser radiation 2, and x and also y denote two mutually orthogonal coordinates in a plane perpendicular to the direction of incidence of the laser beam. The person skilled in the art is of course aware that the position of the focus 7 in the cornea 5 can also be three-dimensionally described in other coordinate systems; in particular, the coordinate system does not have to be a system of rectangular coordinates. The fact that the xy scanner 9 deflects about axes at right angles to one another is therefore not compulsory; on the contrary, use may be made of any scanner which is able to adjust the focus 7 in a plane in which the axis of incidence of the optical radiation does not lie. Systems of oblique coordinates are thus also possible.

Furthermore, systems of non-rectilinear coordinates can also be used to describe or control the position of the focus 7, as will also be commented on hereinafter in greater detail. Examples of coordinate systems of this type are spherical coordinates and also cylindrical coordinates.

For controlling the position of the focus 7, the xy scanner 9 and also the z scanner 11, which jointly form a specific example of a three-dimensional focus shifting device, are activated by a controller 12 via lines which are not designated. The same applies to the laser 8. The controller 3 ensures a suitably synchronous operation of the laser 8 and also of the three-dimensional focus shifting device, implemented in exemplary fashion by the xy scanner 9 and also the z scanner 11, so that the position of the focus 7 in the cornea 5 is shifted in such a way that ultimately a material of specific volume is isolated, the subsequent removal of volume effecting a desired correction of defective vision.

The controller 12 operates in accordance with predefined control data which define the target points for the focus shifting. The control data are generally summarised in a set of control data. In one embodiment, the set of control data defines the coordinates of the target points as a pattern, wherein the sequence of the target points in the set of control data defines the sequential arrangement of the focus positions and thus ultimately a path curve (referred to in the present document also as a path for short). In one embodiment, the set of control data contains the target points as specific setting values for the focus position shifting mechanism, for example for the xy scanner 9 and the z scanner 11. For preparing the ophthalmic surgical method, i.e. before the actual surgical method is executed, the target points and preferably also the order thereof are determined in the pattern. The surgical intervention must be pre-planned in such a way that the control data for the treatment device 1 are defined, the application of which data then achieves a correction of defective vision that is optimal for the patient 4.

The first step is to define the volume which is to be isolated from the cornea 5 and subsequently to be removed. As previously described with reference to FIG. 1a, this requires the need for correction to be ascertained. FIG. 4 shows in subfigures a), b) and c) the optical conditions in the eye 3 of the patient 4. Without defective vision correction, the situation is that shown in subfigure a). The cornea 5 effects together with the lens 13 of the eye a focusing of an object lying at infinity into a focus F positioned on the z axis after the retina 14. The imaging effect derives in this case on the one hand from the lens 13 of the eye, which lens is relaxed when the eye is not accommodated, and also on the other hand from the cornea 5 of the eye that is defined substantially by a front face 15 of the cornea and also a back 16 of the cornea and likewise has an imaging effect on account of its curvature. The optical effect of the cornea 5 is caused by the radius of curvature $R_{CV}$ of the front surface of the cornea. Subfigure a) represents the defective vision merely in exemplary fashion; in reality, the above-mentioned more complex defective visions may be present. However, the following description applies to them too, although some of the specified equations may then contain an additional angle dependency even if reference is not expressly made thereto.

For correcting defective vision, a front lens 17 in the form of a pair of spectacles is placed in a known manner, as illustrated in subfigure b) of FIG. 4, before the eye 3 at a distance $d_{HS}$ from the vertex of the cornea 5. The diffractive power $B_{BR}$ of the lens 17 is adapted such that the lens shifts the far point of the system as a whole, i.e. the system made up of the pair of spectacles and eye, from the focus point F to the corrected focus point F* which is positioned on the retina 14.

With regard to the nomenclature used in this description, it should be noted that the addition of an asterisk to variables indicates that they are variables obtained after a correction. The focus F* is therefore that focus which is present after the optical correction which is achieved in subfigure b) of FIG. 4 by the lens 17 of the pair of spectacles.

Under the justified assumption that a change in thickness of the cornea 5 mainly modifies the radius of curvature of the air-facing anterior surface 15 of the cornea, but not the radius of curvature of the posterior surface 16 of the cornea facing the interior of the eye, the radius of curvature $R_{CV}$ of the anterior surface 15 of the cornea is modified by the removal of the volume. The cornea 5 reduced by the volume has an imaging effect which is altered in such a way that the focus F*, which is then corrected, lies on the retina 14. After the correction an altered anterior surface 15* of the cornea is present, and a correction of defective vision is achieved even without a pair of spectacles.

The curvature to be achieved of the modified anterior surface 15* of the cornea is therefore determined for defining the pattern of the target points. In this case, the starting point is the refractive power of the lens 17 of the pair of spectacles, as determining the corresponding parameters is a standard method in ophthalmic optics. The following formula applies to the refractive power $B_{BR}(q)$ of the lens 17 of the pair of spectacles:

$$B_{BR}(\varphi) = Sph + Cyl \cdot \sin^2(\varphi - \theta). \quad (1)$$

In this equation Sph and Cyl denote the correction values to be implemented of spherical and astigmatic refractive defects respectively and θ denotes the position of the cylinder axis of the cylindrical (astigmatic) defective vision, such as they are known to the person skilled in the art in optometry. Finally, the parameter φ refers to a system of cylindrical coordinates of the eye and is counted anticlockwise looking onto the eye, such as is conventional in ophthalmic optics. Now, with the value $B_{BR}$, the curvature of the modified anterior surface 15* of the cornea is set as follows:

$$R_{CV}^* = 1/((1/R_{CV}) + B_{BR}/((n_c - 1) \cdot (1 - d_{HS} \cdot B_{BR}))) + F \quad (2)$$

In Equation (2) $n_c$ denotes the refractive index of the material of the cornea. The respective value is usually 1.376; $d_{HS}$ denotes the distance at which a pair of spectacles having the refractive power $B_{BR}$ must be positioned from the corneal apex in order to generate the desired correction of defective vision by means of the pair of spectacles; $B_{BR}$ denotes the aforementioned refractive power of the pair of spectacles according to Equation (1). The indication for the refractive power $B_{BR}$ can also include defective visions extending beyond a normal spherical or cylindrical correction. $B_{BR}$ (and thus automatically also $R_{CV}^*$) then have additional coordinate dependencies.

The correction factor F takes account of the optical effect of the change in thickness of the cornea and may be regarded in the first approximation as a constant factor. For a high-precision correction, the factor can be calculated in accordance with the following equation:

$$F = (1 - 1/n_c) \cdot (d_C^* - d_C). \quad (3)$$

$d_C$ and $d_C^*$ are in this case the thickness of the cornea before and after the optical correction respectively. For precise determination, $R_{CV}^*$ is calculated iteratively in that in the $i^{th}$ calculation the variable $(d_C^* - d_C)$ is concluded from the difference $(R_{CV}^* - R_{CV})$ and the corresponding result obtained therefrom for the change in thickness is applied in the $(i+1)^{th}$ calculation. This can be carried out until a termination criterion is met, for example if the difference of the result for the change in thickness is in two successive iterations steps below a correspondingly defined limit. This limit can be defined via a constant difference, for example, corresponding to a precision of the refractive correction that is appropriate for the treatment.

If the change in thickness of the cornea of the eye is disregarded (as is entirely permissible for a simplified method), the correction value F in Equation (2) can be set to zero for a simplified calculation, i.e. disregarded and omitted. Surprisingly, the following simple equation is obtained for the refractive power of the modified cornea 5*:

$$B_{CV}^* = B_{CV} + B_{BR}/(1 - B_{BR} \cdot d_{HS})$$

This equation provides the person skilled in the art in a simple manner, by means of the equation $B_{CV}^* = (n-1)/R_{CV}^*$, with the radius $R_{CV}^*$ of the anterior surface 15* of the cornea that must be present after the modification in order to obtain the desired correction of defective vision, as follows: $R_{CV}^* = 1/((1/R_{CV}) + B_{BR}/((n_c - 1) \cdot (1 - d_{HS} \cdot B_{BR})))$.

For the volume, the removal of which effects the foregoing change in curvature of the anterior surface 15 of the cornea, the border face isolating the volume is now defined. In this regard, account must preferably be taken of the fact that the diameter of the region to be corrected, and thus the diameter of the volume to be removed, should if possible extend over the size of the pupil of the dark-adapted eye.

In a first variant, numerical methods known to the person skilled in the art are used to define a free face circumscribing a volume, removal of which effects the change in curvature. For this purpose, the change in thickness required for the desired modification of curvature is determined along the z axis. This provides the volume as a function of r, φ (in cylindrical coordinates) and this in turn provides the border face thereof.

A simple analytical calculation leads to the following second variant in which the border face of the volume is constructed by two face parts: an anterior face part facing the surface 15 of the cornea and an opposing posterior face part. FIG. 5 shows the corresponding conditions. The volume 18 is bounded towards the anterior surface 15 of the cornea by an anterior cut face 19 positioned at a constant distance $d_F$ below the anterior surface 15 of the cornea. This anterior cut face 19 is also referred to, by analogy with a laser keratome, as a flap face 19, as it serves to allow in the cornea 5 of the eye a lamella in the form of a flap to be lifted, in combination with an opening cut toward the edge, from the underlying cornea 5. This type of removal of the previously isolated volume 18 is of course also possible here.

The anterior cut face 19 has a course of curvature which is positioned by $d_F$ below the anterior surface 15 of the cornea. If the anterior surface is spherical during the surgery, a radius of curvature which is less than the radius of curvature $R_{CV}$ by $d_F$ can be specified for the flap face 19. As will be described hereinafter for preferred variants, a contact glass can ensure when generating the cut face 19 that the anterior surface 15 of the cornea is spherical at the moment when the cut face is generated, so that the pattern of the target points generates a spherical cut face. Although the relaxation of the eye 3 after the detachment of the contact glass may then lead to a non-spherical cut face 19, it is still at a constant distance from the anterior surface 15 or 15* of the cornea.

Posteriorly, the volume 18 which is to be removed from the cornea 5 is bounded by a posterior cut face 20 which is generally not at a constant distance from the anterior surface 15 of the cornea. The posterior cut face 20 will therefore be embodied in such a way that the volume 18 has the form of a lenticule, for which reason the posterior cut face 20 is also referred to as the lenticule face 20. In FIG. 5 the posterior cut face is illustrated, by way of example for a correction of myopia, as a likewise spherical face having a radius of curvature $R_L$, wherein the centre of this curvature generally does not coincide with the centre of curvature of the anterior surface 15 of the cornea, which is likewise spherical in FIG. 5. In a correction of hyperopia, $R_L$ is greater than $R_{CV}-d_F$.

FIG. 6 shows the conditions after removal of the volume 18. The radius of the modified anterior surface 15* of the cornea is now $R_{CV}^*$ and can be calculated in accordance with the equations described hereinbefore, for example. The central thickness $d_L$ of the removed volume 18 is in this case decisive for the change in radius, as FIG. 7 illustrates. In this figure the height $h_F$ of the spherical cap defined by the anterior cut face 19, the height $h_L$ of the spherical cap defined by the posterior cut face 20, and also the thickness $d_L$ of the volume 18 to be removed are also indicated as further variables.

The posterior cut face 20 defines, on account of the constant distance between the anterior surface 15 of the cornea and the anterior cut face 19, the course of curvature of the anterior surface 15* of the cornea after removal of the volume 18. Thus, the posterior cut face 20 will have an angle-dependent radius of curvature, for example in a correction of defective vision taking into account cylindrical parameters. For the lenticule face 20 shown in FIG. 7, the following generally applies:

$$R_L(\varphi)=R_{CV}^*(\varphi)-d_F,$$

or in cylindrical coordinates (z, r, φ)

$$z_L(r,\varphi)=R_L(\varphi)-(R_L^2(\varphi)-r^2)^{1/2}+D_L+D_F.$$

When not taking account of an astigmatism, the dependency on φ is dispensed with and the lenticule face 20 is spherical. However, starting from the need for a cylindrical correction of defective vision, the lenticule face 20 generally has different radii of curvature on various axes, the radii of curvature mostly having the same vertex of course.

Furthermore, this automatically makes it clear that, in the case of a myopic cylindrical correction, the theoretical line of intersection between the flap face 19 and lenticule face 20 does not lie in one plane, i.e. at constant z coordinates. The smallest radius of curvature of the lenticule face 20 is at $\varphi=\theta+\pi/2$; the largest is of course on the axis θ of cylindrical defective vision, i.e. at $\varphi=\theta$. Unlike in the illustration of FIG. 7, in a correction of defective vision, the vertices of the flap face 19 and lenticule face 20 theoretically coincide and the lenticule face 20 is curved more intensively than the flap face 19. The thickness $d_L$ of the lenticule is obtained as the central lenticule thickness in myopia.

In the case of the correction of myopia, the volume 18, which is to be regarded as a lenticule, theoretically has a line of intersection of the lenticule face 20 and flap face 19 at the edge. In the correction of hyperopia, a finite edge thickness is always provided, as the lenticule face 20 is curved less intensively than the flap face 19. However, in this case, the central lenticule density is theoretically equal to zero.

In addition to the flap face 20 and the lenticule face 19, an additional edge face is provided that bounds the bounded volume 18 of the flap face 20 and the lenticule face 19 at the edge. The cutting of this edge face is also executed using the pulsed laser beam. The structure of the edge face will be described hereinafter with reference to FIGS. 12a-c.

In the correction of hyperopia, a finite edge thickness is always provided, as the lenticule face 20 is curved less intensively than the flap face 19. However, in this case, the central lenticule density is theoretically equal to zero. In addition to the flap face 20 and the lenticule face 19, an additional edge face is therefore provided that closes off the volume 18 bounded by the flap face 20 and the lenticule face 19 at the edge. The cutting of this edge face is also executed using the pulsed laser beam.

The embodiment shown in the figures of the volume 18 as being bounded by an anterior cut face 19 at a constant distance from the front face 15 of the cornea and also a posterior cut face 20 is just one option for bounding the volume 18. However, it has the advantage that the optical correction is defined substantially by just one face (the lenticule face 20), so that the analytical description of the other face part of the border face is simpler.

Furthermore, optimum safety margins are provided with regard to the distance of the volume from the anterior surface 15 of the cornea and posterior surface 16 of the cornea. The remaining thickness $d_F$ between the anterior cut face 19 and the anterior surface 15 of the cornea can be set to a constant value of from 50 to 200 µm, for example. In particular, it can be selected in such a way that the pain-sensitive epithelium remains in the lamella formed by the flap face 19 below the anterior surface 15 of the cornea. The formation of the spherical flap face 19 is also in line with previous keratometer cuts; this is advantageous for the acceptance of the method.

After generating the cut faces 19 and 20, the volume 18 thus isolated is then removed from the cornea 5. This is schematically represented in FIG. 8 which further shows that the cut faces 19 and 20 are generated under the action of the treatment laser beam incident in a focus cone 21, for example by sequential arrangement of plasma bubbles, so that in a preferred embodiment the flap cut face 19 and the lenticule cut face 20 are generated by suitable three-dimensional shifting the focus position of the pulsed laser radiation 2.

However, alternatively, in a simplified embodiment it is possible for merely the flap face 19 to be formed by target points defining the curved cut face 19 at a constant distance from the anterior surface 15 of the cornea by pulsed laser radiation and for the volume 18 to be removed by laser ablation, for example using an excimer laser beam. For this purpose, the lenticule face 20 can be defined as a border face of the removal, although this is not mandatory. The treatment device 1 then works like a known laser keratome; nevertheless, the cut face 19 is generated on a curved cornea. The features described hereinbefore and hereinafter respectively are also possible in such variants, in particular as far as the determination of the boundary face, its geometric definition and the determination of control parameters is concerned.

If both the lenticule face 20 and the flap face 19 are generated by pulsed laser radiation, it is expedient to form the lenticule face 20 before the flap face 19, as the optical result in the lenticule face 20 is better (or even may be achieved only) if no alteration of the cornea 5 has yet occurred above the lenticule face 20.

The removal of the volume 18 isolated by the pulsed laser radiation can be achieved, as indicated in FIG. 8, by an edge cut 22 allowing the volume 18 to be extracted in the direction of an arrow 23 shown in FIG. 8. However, alternatively, the edge cut 22 can be embodied in such a way that it connects the anterior cut face 19, i.e. the flap face 19, in the form of a ring to the anterior surface 15 of the cornea, although the edge cut does not extend all the way round an angle of 360°. The lamella isolated in this way remains connected to the remaining tissue of the cornea 5 in a narrow region. This connecting bridge then serves as a hinge, so as to be able to fold the otherwise isolated lamella away from the cornea 5 and to detach the already isolated volume 18 made accessible in this manner from the remainder of the cornea 5 of the eye. The position of the connecting bridge can be predefined when generating the control data or the target points respectively. From this point of view, the described procedure or device therefore isolates the volume 19 within the cornea 5 and generates a lamella, connected to the remainder of the cornea of the eye via a tissue bridge, as a lid over the volume. The lid can be folded away and the volume 18 can be removed.

To generate the cut faces 19 and 20, the target points can now be arranged in a broad range of ways. The prior art, for example WO 2005/011546, describes how special spirals, which extend for example in the manner of a helical line about a main axis lying substantially perpendicularly to the optical axis (z axis), can be used to generate cut faces in the cornea of the eye. The use of a scanning pattern, which arranges the target points in lines, is also known (cf. WO 2005/011545). It goes without saying that these options can be used to generate the above-defined cut faces.

The edge face mentioned hereinbefore may be seen in greater detail in FIGS. 9a and 9b. Elements which have already been described with reference to other figures are provided in these figures with the same reference numerals, so that they will not necessarily be described again.

FIG. 9a is a plan view onto the anterior surface 15 of the cornea with the flap face 19 and also the lenticule face 20 (the rim of which is indicated by a dashed line) and also the edge cut 22 in the case of a correction of hyperopia. A zone of transition between the edge of the lenticule face 20 and the flap face 19, which is achieved by an edge face 24, may also be seen in FIG. 9a. This edge face 24 may clearly be seen in FIG. 9b which is a sectional illustration through the illustration of FIG. 9a along the lines A-A.

Now, the lenticule illustrated in FIG. 9b (and similarly in the following FIGS. 10b, 11b and 12a) has a minimum thickness which is located in the region of the axis of vision OA in the case of a hyperopia-correcting lenticule, but is located at the edge of the lenticule in a correction of myopia. The minimum thickness $d_M$ or $d_L$ ensures that the piece of tissue to be removed in the form of the lenticule 18 is sufficiently stable, so that no particles tear off or the piece of tissue does not rupture during removal. The minimum thickness is preferably in the range of from 5 to 50 µm. The lower limit is in this case provided by the layer thickness of the lamella layers from which the cornea of the eye is constructed. Not dropping substantially below a value of 5 µm ensures that the lenticule still has at least one lamella layer at its thinnest point, thus providing sufficient stability.

The edge face 24 effects the transition from the lenticule face 20 to the flap face 19. In this case, it is designed in the embodiment of FIG. 9b as a conical face which is positioned more obliquely than a conical (in the plan view onto FIG. 9a) face, which is oriented perpendicularly to the front face 15 of the cornea or to the flap face 19 extending parallel thereto, would be positioned. The edge cut 22 is positioned at an angle α to the axis of vision OA, which angle results in such perpendicular course relative to the front face of the cornea.

On the other hand, the edge face 24 extends in a more inclined manner, so that the width B, which the edge face 24 has when viewed from above and along in the direction of the optical axis OA, is greater than in the edge cut 22, for example. The corresponding angle θ is accordingly also larger than the angle α.

FIGS. 10a and 10b show the corresponding conditions in the case of a myopic lenticule, i.e. in the correction of myopia. In this case too, the edge face 24 is provided for and leads to a finite edge thickness of the lenticule 18 that would not be provided in itself on account of the larger curvature of the lenticule face 20 compared to the flap face 10, as both faces would have, at least in their continuation, a line of intersection, i.e. the edge would end in a line of intersection.

The minimum thickness of the lenticule 18, which is present, in a hyperopic form according to FIG. 9b, on or close to the optical axis OA, occurs therefore in a myopic lenticule according to FIG. 10b at the edge. Accordingly, the minimum thickness $d_M$ is also shown at the edge in FIG. 10b. In this case too, the minimum thickness has the effect that the lenticule is sufficiently stable during removal.

It goes without saying that the sectional illustrations of FIGS. 9b and 10b are descriptive for the lenticule as a whole only when no higher-order correction, in particular no astigmatism, is present. If there is astigmatism, the lenticule face 20 is corrected accordingly so as to differ from sphericity; this also has an effect on the edge face 24 in a manner which is obvious to the person skilled in the art.

Figures 11A, 11B:
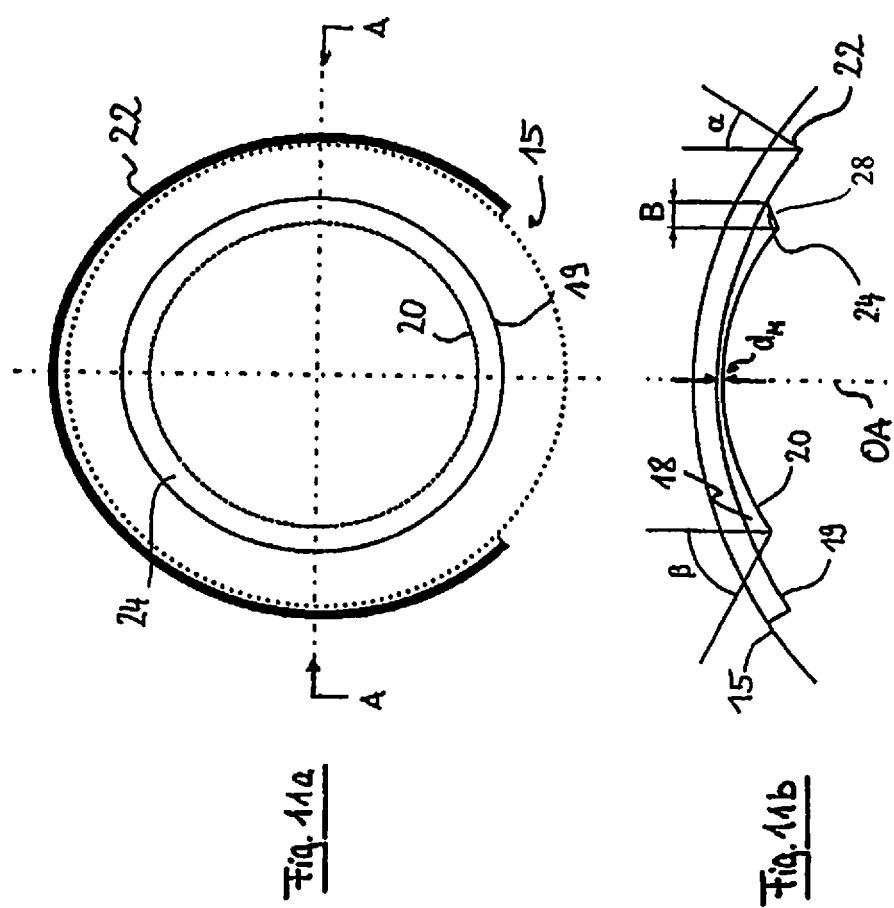

Finally, FIGS. 11a and 11b show conditions corresponding to those of FIGS. 9a and 9b; however, in this case, the edge cut 22, which is generated to expose the lenticule 18, extends over a very much larger angular range than in FIGS. 9 and 10.

FIGS. 9 to 11 show an edge face 24 defining cut curve 28 which is designed as an oblique cut. However, the edge face 24 can also have a structure differing from such a course which is linear viewed in cross section. This is shown by way of example in FIGS. 12a to d. In these figures, FIG. 12a represents a sectional illustration similar to that of FIG. 9b, 10b or 11b. FIGS. 12b to 12d are enlarged views of the detail indicated by a dotted line in FIG. 12a and represent different options for the structure of the edge face 24.

According to FIG. 12b the edge face 24 defining cut curve 28 consists of two portions 25 and 26 which are substantially linear in cross section. The first portion 25 runs perpendicularly into the flap face 19. The height of the first portion 25 effects a thickness $d_R$ of the edge. This thickness is preferably selected so as to be in the range of from 5 to 10 µm and ensures that fragments do not become torn off in the region of the edge face 24 when the lenticule 18 is removed. Such fragments would have very disadvantageous effects on ingrowth and would lead to undesirable regression. In order to achieve, despite the first portion 25 lying perpendicularly to the flap face 19, a smooth positioning of the corneal lamella 27 isolated by the flap cut 19 when the lenticular volume was removed, the second portion 26 of the edge face 24 has in the embodiment of FIG. 12b an oblique course towards the axis of vision. This oblique course provides, in turn, a width B which is much greater than that which would be provided in an edge 24 extending perpendicularly to the flap face 19 throughout.

According to FIG. 12b the edge face 24 consists of two portions 25 and 26 which are substantially linear in cross section. The first portion 25 runs perpendicularly into the flap face 19. The height of the first portion 25 effects a thickness $d_R$ of the edge. This thickness is preferably selected so as to be in the range of from 5 to 10 μm and ensures that fragments do not become torn off in the region of the edge face 24 when the lenticule 18 is removed. Such fragments would have very disadvantageous effects on ingrowth and would lead to undesirable regression. In order to achieve, despite the first portion 25 lying perpendicularly to the flap face 19, a smooth positioning of the corneal lamella 27 isolated by the flap cut 19 when the lenticular volume was removed, the second portion 26 of the edge face 24 has in the embodiment of FIG. 12b an oblique course towards the axis of vision. This oblique course provides, in turn, a width B which is much greater than that which would be provided in an edge 24 extending perpendicularly to the flap face 19 throughout.

FIG. 12c shows a modification of the structure of the edge face 24 of FIG. 12b, in which a continuously curved second portion 26, which rounds off the edge between the lenticule face 20 and the flap face 19 in the region remote from the anterior surface 15 of the cornea of the eye, is formed on the first portion 25 running perpendicularly into the flap face 19. The perpendicular running-in of the first portion 25 ensures, again, a minimum edge thickness $d_R$ which prevents pieces of tissue from becoming torn off from the edge of the lenticule when the lenticular tissue is removed. Preferably, the minimum edge thickness is in the same order of magnitude as the centre thickness $d_M$.

This is also achieved in the edge structure according to FIG. 12d, which is embodied in an S-shaped manner, the first portion 25 running, again, perpendicularly into the flap face 19. On account of the S-shaped structure, the sectional illustration of the edge face 24 has in this configuration a turning point, and the second portion 26 preferably ends likewise at right angles in the lenticule face 20.

The contact glass has the further advantage that the anterior surface 15 of the cornea is also automatically spherical as a result of the pressing onto the spherical underside 26 of the contact glass. Thus, when the contact glass is pressed on, the anterior cut face 19, which is positioned at a constant distance below the anterior surface 15 of the cornea, is also spherical, leading to a greatly simplified control. It is therefore preferable, quite independently of other features, to use a contact glass having a spherical contact glass underside and to bound the volume by an anterior cut face 19 and also a posterior cut face, the anterior cut face being generated as a spherical face at a constant distance $d_F$ below the anterior surface 15 of the cornea. The posterior cut face has a course of curvature corresponding, apart from the distance $d_F$ from the anterior surface of the cornea, to that desired for the correction of defective vision when the eye is relaxed, i.e. after the contact glass has been detached. The same applies to the definition of the target points and to the operating method respectively.

The invention claimed is:

1. A treatment apparatus for surgical correction of defective vision of an eye, the treatment apparatus comprising:

a laser device including a laser, optics and a 3D focus shifting device, wherein the laser device is controlled by a control device and separates corneal tissue of the eye by applying laser radiation;

the control device being programmed with an algorithm that controls an operation of the laser device to emit the laser radiation into the cornea at different focus positions wherein the controlled operation of the laser device isolates a lenticular shaped volume in the cornea, the lenticular volume being structured such that removal of the volume effects the correction of the defective vision; and the control device being programmed with the algorithm that controls the operation of the laser device such that the lenticular volume has a minimum thickness in a range of from 5 to 50 μm at a thinnest part of the lenticular volume, wherein the thinnest part of the lenticular volume is at a location of the lenticular volume which location depends on the defective vision;

wherein when the defective vision comprises myopia, the location of the thinnest part of the lenticular volume is at a peripheral edge of the lenticular volume; and wherein when defective vision comprises hyperopia, the location of the thinnest part of the lenticular volume is at or near an axis of vision of the eye.

2. The apparatus according to claim 1, wherein:

the control device is programmed with the algorithm that controls the operation of the laser device such that the lenticular volume has a posterior face and an anterior face; and the control device further is programmed with the algorithm that controls the laser device such that the anterior face is positioned at a constant distance $d_F$ from the anterior surface of the cornea and the posterior face is curved and has a radius of curvature $R_L = R_{CV}^* - d_F$, wherein $R_{CV}^*$ satisfies the following equation, $$R_{CV}^* = 1/((1/R_{CV}) + B_{BR}(n_c-1) \cdot (1 - d_{HS} \cdot B_{BR})) + F,$$

and $R_{CV}$ is a radius of curvature of the cornea before removal of the volume, $n_c$ is a refractive index of a material of the cornea, F is a correction factor, $B_{BR}$ is a refractive power of a pair of spectacles suitable for correcting defective vision, and also $d_{HS}$ is a distance at which the pair of spectacles having the refractive power $B_{BR}$ would have to be positioned before a corneal apex in order to achieve a desired correction of defective vision by the pair of spectacles.

3. The apparatus according to claim 2, wherein the control device further controls the laser device such that the following applies:

$$F = (1 - 1/n_c) \cdot (d_C^* - d_C),$$

wherein $d_C$ and $d_C^*$ respectively denote a thickness of the cornea before and after removal of the volume and the radius $R_{CV}^*$ can be calculated iteratively in that during each iteration step a change in thickness $(d_C^* - d_C)$ is concluded from the difference $(R_{CV}^* - R_{CV})$ and the corresponding result obtained therefrom for the change in thickness is applied in the calculation of $R_{CV}^*$ in a next iteration step.

4. The apparatus according to claim 2, wherein:

the control device is programmed with the algorithm that controls the operation of the laser device such that the lenticular volume has a posterior face and an anterior face, wherein, in cylindrical coordinates (z, r, φ), the origin of which is positioned at the point at which the axis of vision (OA) passes through the front face of the cornea, the posterior face satisfies the equation $$z_L(r,\varphi)=R_L(\varphi)-(R_L^2(\varphi)-r^2)^{1/2}+d_M+d_F,$$

wherein $d_M$ represents the minimum thickness.

5. The apparatus according to claim 1, wherein:
the control device is programmed with the algorithm that controls the operation of the laser device such that the lenticular volume has a posterior face and an anterior face,
wherein the posterior face and the anterior face have borders that are connected via an edge face,
wherein the edge face forms with a plane in which the axis of vision is contained a cut curve,
wherein the cut curve has an extension that is, when seen perpendicular to the viewing axis, larger than an extension of one of the following two hypothetical lines:
 a straight line extending perpendicularly from the border of the posterior face to the anterior face or to an imaginary continuation of the anterior face; and
 a straight line extending perpendicularly from the border of the anterior face to the posterior face or to an imaginary continuation of the posterior face.

6. The apparatus according to claim 5, wherein the control device further is programmed with the algorithm that controls the laser device such that the edge face has a first portion opening perpendicularly into the anterior face and a second portion inclined more acutely toward the axis of vision.

7. The apparatus according to claim 6, wherein the first portion has a height $d_R$ of more than 5 µm.

8. The apparatus to claim 6, wherein the second portion is positioned at an angle of from 80° to 100° relative to the direction of the axis of vision.

9. The apparatus according to claim 6, wherein the second portion is concave, based on the point at which the axis of vision passes through the front face of the cornea.

10. The apparatus according to claim 6, wherein the defective vision comprises hyperopia and the first portion has a height $d_R$ which is equal to the minimum thickness $d_M$ within limits of cut face accuracy.

11. A method for generating control data for a laser device of a treatment apparatus for surgical correction of defective vision of an eye, wherein the laser device comprises a laser, optics and a 3D focus shifting device, wherein the laser device is controlled according to the control data to separate corneal tissue of the eye by applying laser radiation,
wherein the control data control an operation of the laser device to emit the laser radiation into the cornea at different focus positions wherein the controlled operation of the laser device isolates a lenticular shaped volume in the cornea, the lenticular volume being structured such that removal of the volume effects the correction of the defective vision,
wherein the method further comprises generating a set of control data and storing the set of control data in a memory, the generating comprising:
defining the lenticular volume such that the lenticular volume has a thinnest part of the lenticular volume having a minimum thickness in a range of from 5 to 50 µm, wherein the minimum thickness part is at a location of the lenticular volume which location depends on the defective vision;
wherein when the defective vision comprises myopia, the location of the thinnest part of the lenticular volume is at a peripheral edge of the lenticular volume;
wherein when the defective vision comprises hyperopia, the location of the thinnest part of the lenticular volume is at or near an axis of vision of the eye.

12. The method according to claim 11, wherein:
the control data control the operation of the laser device such that the lenticular volume has a posterior face and an anterior face, and
the control data further control the laser device such that the anterior face is positioned at a constant distance $d_F$ from the anterior surface of the cornea and the posterior face is curved and has a radius of curvature $R_L=R_{CV}^*-d_F$, wherein $R_{CV}^*$ satisfies the following equation:

$$R_{CV}^*=1/((1/R_{CV})+B_{BR}/((n_c-1)\cdot(1-d_{HS}\cdot B_{BR})))+F,$$

and $R_{CV}$ is a radius of curvature of the cornea before removal of the volume, $n_c$ is a refractive index of a material of the cornea, F is a correction factor, $B_{BR}$ is a refractive power of a pair of spectacles suitable for correcting defective vision, and also $d_{HS}$ is a distance at which the pair of spectacles having the refractive power $B_{BR}$ would have to be positioned before a corneal apex in order to achieve a desired correction of defective vision by the pair of spectacles.

13. The method according to claim 12, wherein the control data further control the laser device such that the following applies:

$$F=(1-1/n_c)\cdot(d_C^*-d_C),$$

wherein $d_C$ and $d_C^*$ respectively denote a thickness of the cornea before and after removal of the volume and the radius $R_{CV}^*$ is calculated iteratively in that during each iteration step a change in thickness $(d_C^*-d_C)$ is concluded from the difference $(R_{CV}^*-R_{CV})$ and the corresponding result obtained therefrom for the change in thickness is applied in the calculation of $R_{CV}^*$ in a next iteration step.

14. The method according to claim 12, wherein
the control data control the operation of the laser device such that the lenticular volume has a posterior face and an anterior face,
wherein, in cylindrical coordinates $(z, r, \varphi)$, the origin of which is positioned at the point at which the axis of vision (OA) passes through the front face (15) of the cornea, the posterior face (20) satisfies the equation:

$$z_L(r,\varphi)=R_L(\varphi)-(R_L^2(\varphi)-r^2)^{1/2}+d_M+d_F,$$

wherein $d_M$ represents the minimum thickness.

15. The method according to claim 11, wherein
the control data control the operation of the laser device such that the lenticular volume has a posterior face and an anterior face,
wherein the posterior face and the anterior face have borders that are connected via an edge face,
wherein the edge face forms with a plane in which the axis of vision is contained a cut curve,
wherein the cut curve has an extension that is, when seen perpendicular to the viewing axis, larger than an extension of one of the following two hypothetical lines:
 a straight line extending perpendicularly from the border of the posterior face to the anterior face or to an imaginary continuation of the anterior face; and
 a straight line extending perpendicularly from the border of the anterior face to the posterior face or to an imaginary continuation of the posterior face.

16. The method according to claim 15, wherein the control data control the laser device such that the edge face has a first portion opening perpendicularly into the anterior face and a second portion inclined more acutely toward the axis of vision.

17. The method according to claim 16, wherein the first portion has a height $d_R$ of more than 5 µm.

18. The method according to claim 17, wherein the first portion has the height $d_R$ of at least 10 μm.

19. The method to claim 16, wherein the second portion is positioned at an angle of from 80° to 100° relative to the direction of the axis of vision.

20. The method according to claim 16, wherein the second portion is concave, based on the point at which the axis of vision passes through the front face of the cornea.

21. The method according to claim 16, wherein the defective vision comprises hyperopia and the first portion has a height $d_R$ which is equal to the minimum thickness $d_M$ within limits of cut face accuracy.

22. A method for surgical correction of defective vision of an eye, the method comprising:
    separating corneal tissue by applying a laser radiation and isolating a lenticular volume thereby;
    removing the isolated lenticular volume from in the cornea, the removal of the lenticular volume effecting the correction of the defective vision,
    the method further comprising:
    isolating the lenticular volume such that the lenticular volume has a thinnest part of the lenticular volume having a minimum thickness in a range of from 5 to 50 μm, wherein the thinnest part of the lenticular volume is at a location of the lenticular volume which location depends on the defective vision; and
    wherein when the defective vision comprises myopia, the location of the thinnest part of the lenticular volume is at a peripheral edge of the lenticular volume; and
    wherein when the defective vision comprises hyperopia, the location of the thinnest part of the lenticular volume is at or near an axis of vision of the eye.

23. The method according to claim 22, wherein:
    the lenticular volume has a posterior face and an anterior face, and
    the anterior face is positioned at a constant distance $d_F$ from the anterior surface of the cornea and the posterior face is curved and has a radius of curvature $R_L = R_{CV}^* - d_F$, wherein $R_{CV}^*$ satisfies the following equation:

$$R_{CV}^* = 1/((1/R_{CV}) + B_{BR}/((n_c-1)\cdot(1-d_{HS}\cdot B_{BR}))) + F,$$

and $R_{CV}$ is a radius of curvature of the cornea before removal of the volume, $n_c$ is a refractive index of a material of the cornea, F is a correction factor, $B_{BR}$ is a refractive power of a pair of spectacles suitable for correcting defective vision, and also $d_{HS}$ is a distance at which the pair of spectacles having the refractive power $B_{BR}$ would have to be positioned before a corneal apex in order to achieve a desired correction of defective vision by the pair of spectacles.

24. The method according to claim 22, wherein the following applies:

$$F = (1-1/n_c)\cdot(d_C^* - d_C),$$

wherein $d_C$ and $d_C^*$ respectively denote a thickness of the cornea before and after removal of the volume and the radius $R_{CV}^*$ is calculated iteratively in that during each iteration step a change in thickness $(d_C^* - d_C)$ is concluded from the difference $(R_{CV}^* - R_{CV})$ and the corresponding result obtained therefrom for the change in thickness is applied in the calculation of $R_{CV}^*$ in a next iteration step.

25. The method according to claim 23, wherein:
    the lenticular volume has a posterior face and an anterior face,
    wherein, in cylindrical coordinates (z, r, φ), the origin of which is positioned at the point at which the axis of vision (OA) passes through the front face (15) of the cornea, the posterior face (20) satisfies the equation $$z_L(r,\varphi) = R_L(\varphi) - (R_L^2(\varphi) - r^2)^{1/2} + d_M + d_F,$$

wherein $d_M$ represents the minimum thickness.

26. The method according to claim 22, wherein:
    the lenticular volume has a posterior face and an anterior face,
    wherein the posterior face and the anterior face have borders that are connected via an edge face,
    wherein the edge face forms with a plane in which the axis of vision is contained a cut curve,
    wherein the cut curve has an extension that is, when seen perpendicular to the viewing axis, larger than an extension of one of the following two hypothetical lines:
    a straight line extending perpendicularly from the border of the posterior face to the anterior face or to an imaginary continuation of the anterior face,
    a straight line extending perpendicularly from the border of the anterior face to the posterior face or to an imaginary continuation of the posterior face.

27. The method according to claim 26, wherein the control data control the laser device such that the edge face has a first portion opening perpendicularly into the anterior face and a second portion inclined more acutely toward the axis of vision.

28. The method according to claim 27, wherein the first portion has a height $d_R$ of more than 5 μm.

29. The method according to claim 28, wherein the first portion has the height $d_R$ of at least 10 μm.

30. The method to claim 27, wherein the second portion is positioned at an angle of from 80° to 100° relative to the direction of the axis of vision.

31. The method according to claim 27, wherein the second portion is concave, based on the point at which the axis of vision passes through the front face of the cornea.

32. The method according to claim 27, wherein the defective vision comprises hyperopia and the first portion has a height $d_R$ which is equal to the minimum thickness $d_M$ within limits of cut face accuracy.

33. The apparatus according to claim 7, wherein the first portion has the height $d_R$ of at least 10 μm.

* * * * *

UNITED STATES PATENT AND TRADEMARK OFFICE
CERTIFICATE OF CORRECTION

PATENT NO. : 10,682,256 B2
APPLICATION NO. : 14/804943
DATED : June 16, 2020
INVENTOR(S) : Mark Bischoff et al.

Page 1 of 1

It is certified that error appears in the above-identified patent and that said Letters Patent is hereby corrected as shown below:

In the Claims

Column 18, Line 38, delete the existing equation and insert the following equation:
--$R_{CV}^* = 1 / ((1/R_{CV}) + B_{BR} / ((n_c-1) \cdot (1 - d_{HS} B_{BR}))) + F$,--

Signed and Sealed this
Twenty-fifth Day of August, 2020

Andrei Iancu
*Director of the United States Patent and Trademark Office*